United States Patent
Hodson et al.

(10) Patent No.: US 9,662,211 B2
(45) Date of Patent: May 30, 2017

(54) HEART VALVE TESTING APPARATUS AND METHODS

(71) Applicant: VIVITRO LABS INC., Victoria (CA)

(72) Inventors: Ted Hodson, Victoria (CA); Satyaprakash Karri, Victoria (CA); Scott Phillips, Victoria (CA)

(73) Assignee: VIVITRO LABS INC., Victoria, CA (US)

( * ) Notice: Subject to any disclaimer, the term of this patent is extended or adjusted under 35 U.S.C. 154(b) by 217 days.

(21) Appl. No.: 14/404,989

(22) PCT Filed: Jun. 25, 2013

(86) PCT No.: PCT/CA2013/050496
§ 371 (c)(1),
(2) Date: Dec. 2, 2014

(87) PCT Pub. No.: WO2014/000105
PCT Pub. Date: Jan. 3, 2014

(65) Prior Publication Data
US 2015/0128684 A1    May 14, 2015

Related U.S. Application Data

(60) Provisional application No. 61/664,107, filed on Jun. 25, 2012.

(51) Int. Cl.
*A61F 2/24*     (2006.01)
*G01M 99/00*    (2011.01)

(52) U.S. Cl.
CPC .......... *A61F 2/2472* (2013.01); *G01M 99/00* (2013.01)

(58) Field of Classification Search
CPC  A61F 2/24; A61F 2/2472; A61F 2/00; G01M 99/00
See application file for complete search history.

(56) References Cited

U.S. PATENT DOCUMENTS 3,185,169 A * 5/1965 Bruun ................ G05D 16/0619
137/98
4,450,710 A    5/1984 Nettekoven
(Continued)

FOREIGN PATENT DOCUMENTS

WO    2010102185 A2    9/2010
WO    2011087830 A2    7/2011

OTHER PUBLICATIONS

"Testing methods for artificial heart valves—bulk qualities", Medical University Berlin, http://www.charite.de/biofluidmechanik/en/research/fields_1.html, 2010.

*Primary Examiner* — Nguyen Ha
(74) *Attorney, Agent, or Firm* — Oyen Wiggs Green & Mutala LLP (57) ABSTRACT

Methods and apparatus for accelerated wear testing of prosthetic heart valves apply non-sinusoidal pressure waveforms. The waveforms may maintain a threshold reverse pressure for a desired duration while limiting a peak reverse pressure. Apparatus may include a fluid impeller such as a bellows or a piston driven by an actuator having a position controlled by a motion control system. The apparatus may include a pressure control system comprising one or more bypass channels and bypass valves controlling a resistance of the bypass channels to fluid flow. The bypass valves may be controlled in real time.

34 Claims, 4 Drawing Sheets

(56) References Cited

U.S. PATENT DOCUMENTS

| | | | |
|---|---|---|---|
| 4,546,642 | A | 10/1985 | Swanson |
| 4,682,491 | A | 7/1987 | Pickard |
| 5,176,153 | A | 1/1993 | Eberhardt |
| 5,272,909 | A | 12/1993 | Nguyen et al. |
| 5,326,371 | A | 7/1994 | Love et al. |
| 5,531,094 | A | 7/1996 | More et al. |
| 5,531,784 | A | 7/1996 | Love et al. |
| 5,584,878 | A | 12/1996 | Love et al. |
| 5,670,708 | A | 9/1997 | Vilendrer |
| 5,899,937 | A | 5/1999 | Goldstein et al. |
| 5,961,549 | A | 10/1999 | Nguyen et al. |
| 6,062,075 | A | 5/2000 | Ritz et al. |
| 6,245,105 | B1 | 6/2001 | Nguyen et al. |
| 6,413,275 | B1 | 7/2002 | Nguyen et al. |
| 6,881,224 | B2 | 4/2005 | Kruse et al. |
| 7,326,564 | B2 | 2/2008 | Lundell et al. |
| 2010/0225478 | A1 | 9/2010 | McCloskey et al. |
| 2010/0281994 | A1* | 11/2010 | Brown ............... G01L 19/0645 73/729.1 |
| 2011/0132073 | A1 | 6/2011 | McCloskey et al. |
| 2011/0303026 | A1 | 12/2011 | Lee |

\* cited by examiner

HEART VALVE TESTING APPARATUS AND METHODS

TECHNICAL FIELD

This application relates to apparatus and methods for testing replacement heart valves (e.g. prosthetic heart valves). Some embodiments perform accelerated wear testing.

BACKGROUND

Prosthetic heart valves are normally tested for durability in accordance with the ISO5840 standard which calls for 200 million cycles of testing. In order to achieve these huge cycle numbers in a reasonable time the cycle rate may be set to 1200 cycles per minute or more. The standard requires that a certain proportion of each cycle (e.g. 5%) be at or above a certain reverse pressure.

It is difficult to perform accelerated tests that comply with the requirements of ISO 5840 and other standards because many common valves are made from animal tissue and are quite flexible. This fact combined with the high cycle rate and fluid dynamic effects can make it hard to test heart valves in a manner that complies with applicable standards.

Excess reverse pressure can cause heart valves to fail prematurely. Some valve testing apparatus causes pressure spikes or applies other excess pressures which can result in false testing failures.

There is a need for methods and apparatus for testing heart valves that are reliable and operate according to desired testing protocols. There is also a need for methods and apparatus capable of executing new testing protocols that may provide enhanced information about the long term reliability of heart valves being tested.

SUMMARY

This invention has a number of aspects. One aspect provides apparatus for testing replacement heart valves that comprises a fluid impeller such as a bellows or piston that is reciprocated in a non-sinusoidal trajectory. Another aspect provides apparatus for testing replacement heart valves that comprises a bypass and a controllable bypass valve that is controlled to limit reverse pressures applied to a heart valve under test. Another aspect provides apparatus for testing replacement heart valves that includes a pressure control system comprising compliance devices upstream and/or downstream of a heart valve under test. Another aspect provides methods for testing replacement heart valves.

An example aspect provides apparatus for testing replacement heart valves. The apparatus comprises a mounting structure for supporting a heart valve in a passage extending between first and second chambers and a driving system for driving the flow of fluid through a heart valve supported on the mounting structure. The driving system comprises an actuator and a controller connected to control the actuator to provide a desired non-sinusoidal motion to a fluid impeller.

In example embodiments the fluid impeller comprises a piston or a bellows. The actuator may comprise a linear or rotary actuator. In some embodiments the actuator comprises a servo motor. Where the actuator comprises a rotary actuator the apparatus may comprise a rotary-to-linear motion converter driven by the rotary actuator and connected to drive the fluid impeller. The rotary-to-linear converter may, for example comprise a screw or a cam.

In some embodiments the driving system comprises a position sensor connected to monitor a position of the fluid impeller. The controller may comprise a position-feedback controller or a position and velocity feedback controller.

The controller may comprise one or more of the following features:
- a motion control system that is configurable to operate the actuator to provide a desired profile of position as a function of time.
- the controller is configured to provide control over one or more of: the amplitude of motions driven by the actuator; the frequency of the motions driven by the actuator; and the waveform of the wave input provided by motions driven by the actuator.
- the controller is configured to control the actuator to move the fluid impeller according a first profile having a first shape when the fluid impeller is moving in a direction such that the heart valve is closed and to move the fluid impeller according a second profile having a second shape different from the first shape when the fluid impeller is moving in a direction such that the heart valve is open.
- the controller is configured to execute an algorithm that uses feedback of pressure measured on one or both sides of the valve under test to provide proportional control of the drive wave shape to minimize pressures experienced by the test valve during the full closed cycle while achieving a threshold reverse pressure for at least a specified portion of each cycle.
- the controller is configured to execute a learning algorithm that automatically tunes parameters that define the waveform with which the actuator is driven to achieve a desired pressure profile at the valve under test.
- the controller is configured to provide a plurality of operator selectable, preprogrammed wave forms.
- a user interface or API configured to permit a user to tailor the waveforms to achieve a desired wave shape, amplitude and/or frequency.

The inventive apparatus may comprise a pressure control system. The pressure control system may comprise a bypass providing a fluid connection between the first and second chambers and one or more bypass valves controllable to regulate a flow of fluid through the bypass. The one or more bypass valves may provide resistance to fluid flow that is set manually and/or a resistance of the one or more bypass valves to fluid flow may be automatically controlled.

The apparatus may comprise one or more pressure sensors. The controller may be configured to monitor fluid pressure at the one or more pressure sensors and to control the one or more bypass valves and/or the motion of the fluid impeller based on the monitored fluid pressure.

In some embodiments the controller is configured to operate the driving system such that a reverse pressure on the heart valve rises to a target peak pressure somewhat in excess of a reverse threshold pressure more slowly than a sinusoidal waveform would and holds at a pressure exceeding the reverse threshold pressure for longer than a sinusoidal waveform having the same target peak pressure.

Another example aspect provides apparatus for testing replacement heart valves. The apparatus comprises a mounting structure for supporting a heart valve in a passage extending between first and second chambers and a driving system for driving the flow of fluid through a heart valve supported on the mounting structure. The driving system comprises an actuator operable to move the fluid impeller to, in a first period, cause a flow of fluid through a heart valve under test in a forward direction wherein the heart valve is open; and, in a second period cause a flow of fluid in a reverse direction that causes the heart valve to close and applies a reverse pressure to the heart valve. The apparatus comprises a pressure control system comprising a bypass extending between the first and second chambers, a bypass valve in the bypass, the bypass valve controllable to alter a resistance of the bypass valve to fluid flow and a pressure sensor. A controller is configured to control the bypass valve in response to a pressure sensed by the pressure sensor to limit the reverse pressure applied to the heart valve in the second period.

Another example aspect provides a method for testing replacement heart valves. The method comprises controlling an actuator to, in a first period, cause a flow of fluid through a heart valve under test in a forward direction wherein the heart valve is open; and in a second period cause a flow of fluid in a reverse direction that causes the heart valve to close and applies a reverse pressure to the heart valve. In the second period, the actuator is controlled to apply a non-sinusoidal pressure waveform to the closed heart valve.

The method may comprise, during the second period, controlling a flow of fluid through a bypass channel so as to limit a reverse pressure on the heart valve. Controlling the flow of fluid through the bypass channel may be performed in real time in response to one or more pressure sensor readings.

Additional aspects of the invention and features of example embodiments are described below and/or illustrated in the accompanying drawings.

BRIEF DESCRIPTION OF THE DRAWINGS

The accompanying drawings illustrate non-limiting example embodiments of the invention.

DESCRIPTION

Throughout the following description specific details are set forth in order to provide a more thorough understanding to persons skilled in the art. However, well known elements may not have been shown or described in detail to avoid unnecessarily obscuring the disclosure. The following description of examples of the technology is not intended to be exhaustive or to limit the system to the precise forms of any example embodiment. Accordingly, the description and drawings are to be regarded in an illustrative, rather than a restrictive, sense.

Figure 1:
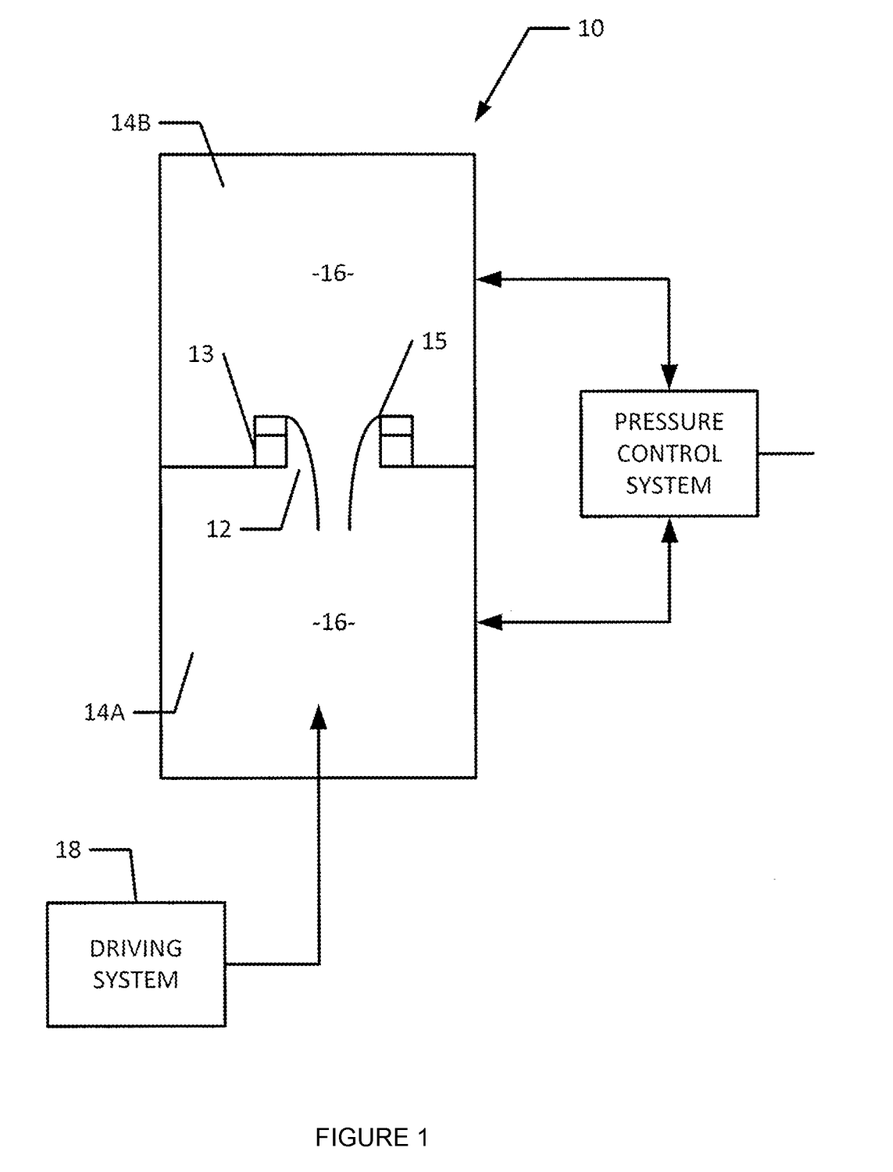
FIG. 1 is a schematic illustration showing a heart valve testing apparatus according to an example embodiment of the invention.

FIG. 1 shows example apparatus 10 for testing the durability of heart valves. Apparatus 10 comprises a passage 12 extending between chambers 14A and 14B. A suitable mounting structure 13 is provided for supporting a heart valve 15 to be tested. Chambers 14A and 14B and passage 12 may contain a suitable fluid 16 such as a saline solution. Heart valve 15 may be tested by controlling the flow of fluid 16 in apparatus 10 such that, in a first phase, heart valve 15 opens to allow fluid 16 to flow through passage 12 in a forward direction and then, in a second phase heart valve 15 closes to block flow of fluid 16 though passage 12 in the reverse direction. In the second phase a reverse pressure is applied to heart valve 15.

This disclosure describes a driving system 18 for driving the flow of fluid through heart valve 15 and also describes a pressure control system 19 for controlling reverse pressure on a heart valve 15. A heart valve testing apparatus may comprise both systems 18 and 19 as described herein. However, a driving system 18 as described herein has application in heart valve testing apparatus which lacks a pressure control system 19 and a pressure control system 19 as described herein may be applied in heart valve testing apparatus that uses driving systems different from driving system 18. The apparatus described herein advantageously includes both a driving system 18 and a pressure control system 19. Pressure control system 19 may operate by actively controlling a bypass whereby fluid 16 can pass between chambers 14A and 14B bypassing valve 15 and/or actively controlling one or more compliance devices which can temporarily receive some fluid 16 and/or actively controlling one or more valves which allow fluid 16 to flow out of chamber 14A and/or 14B.

Figure 2:
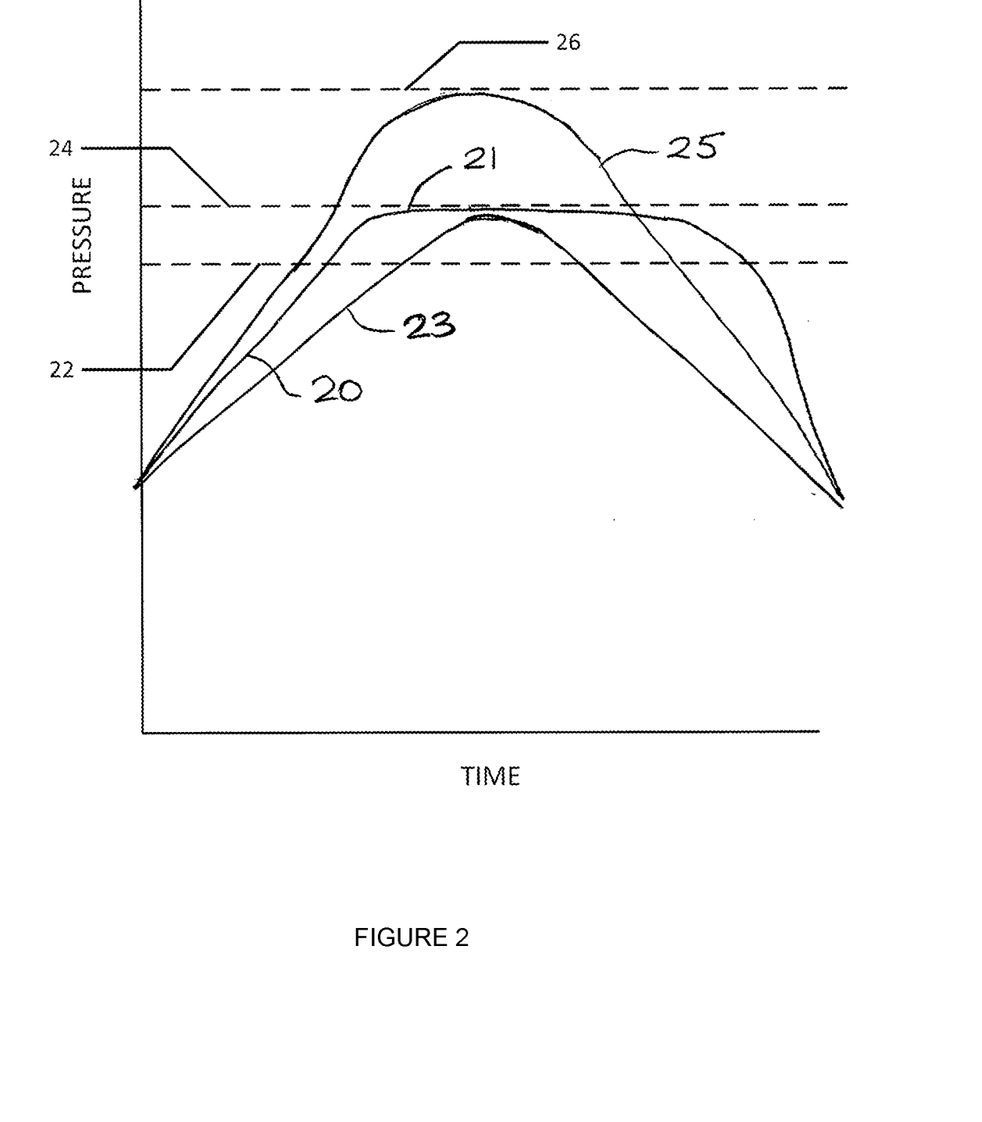
FIG. 2 shows some example waveforms.

Driving system 18 may be configured to cause especially the reverse pressure on heart valve 15 to vary with time in a manner that is non-sinusoidal. Driving system 18 may drive fluid 16 such that reverse pressure on heart valve 15 rises to a target peak pressure somewhat in excess of a reverse threshold pressure more slowly than a sinusoidal waveform would and holds at a pressure exceeding the reverse threshold pressure for longer than a sinusoidal waveform having the same target peak pressure. This is illustrated in FIG. 2. It can be seen that pressure waveform 20 approaches a peak 21 more gradually than a sinusoid 23 (as indicated by a lower slope near peak 21) and then stays at or above the reverse threshold pressure 22 for longer than sinusoid 23, while minimizing the peak pressure 24. To achieve the same duration of pressure exceeding the reverse threshold pressure 22 as provided by a waveform like waveform 20 with a sinusoidal pressure waveform would require a sinusoidal waveform 25 having a significantly higher peak pressure 26. Ideally pressure waveform 20 approaches its peak reverse pressure more slowly than sinusoid 25 while allowing valve 15 to open more quickly than a sinusoidal flow 25 of fluid 16 would provide.

Figure 3:
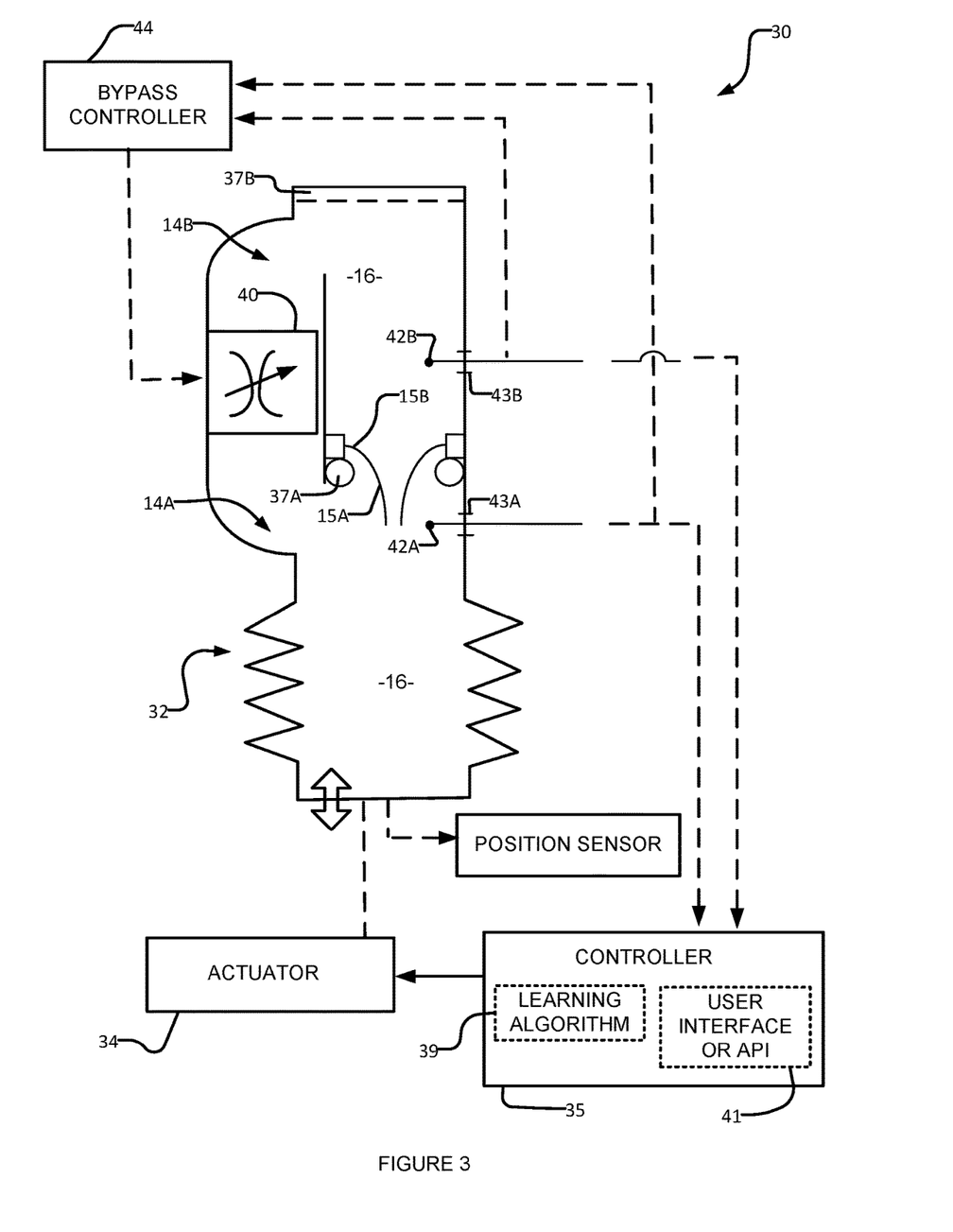
FIG. 3 shows valve testing apparatus according to another example embodiment.

To achieve the desired pressure/fluid flow profiles, driving system 18 may comprise an actuator that is controlled to provide a desired non-sinusoidal motion to a piston, bellows, or the like. FIG. 3 shows apparatus 30 according to an example embodiment wherein driving system 18 comprises a bellows 32 and an actuator 34 which applies a force to compress bellows 32. Compression of bellows 32 causes fluid 16 to apply pressure to the valve 15 under test. On the reverse cycle actuator 34 pulls on bellows 32 which sucks fluid 16 through valve 15. Valve 15 opens to allow the fluid 16 to pass, returning the device to the starting condition and ready for another compression. Bellows 32 may be made from any suitable material. In some embodiments, bellows 32 are made from Inconel.

In some embodiments actuator 34 comprises a servo motor, either linear or rotary. Where actuator 34 comprises a rotary motor then a suitable rotary to linear converter such as a ball screw, a cam or the like may be provided to drive motion of bellows 32. Actuator 34 may comprise alternative structures, such as a voice-coil driver or the like. Actuator 34 is driven by a controller 35 that applies driving electrical signals to actuator 34. The actuating electrical signals result in non-sinusoidal motion of bellows 32 (or of a piston or other alternative fluid-propelling structure).

In some embodiments driving system 18 comprises a position sensor connected to monitor a position of bellows 32 and controller 35 comprises a position-feedback controller or a position and velocity feedback controller. In some embodiments, controller 35 comprises a motor amplifier configured to drive actuator 34 with non-sinusoidal signals.

Controller 35 may comprise a motion control system that is configurable to operate actuator 34 to provide a desired profile of position as a function of time which will result in the desired pressure profile acting on valve 15. Controller 35 may provide control over one or more of the amplitude of motions of actuator 34 or an alternative wave input mechanism that bi-directionally drives fluid through the valve under test; the frequency of the driven motions of actuator 34; and the shape (waveform) of the wave input provided by motions of actuator 34. In some embodiments the shape of the profile of the motion of actuator 34 is different when actuator 34 is moving in a direction such that the valve under test is closed than it is when actuator 34 is moving in a direction such that the valve under test is open.

In some embodiments controller 35 executes an algorithm that uses feedback of pressure measured on one or both sides of a valve under test to provide proportional control of the drive wave shape to minimize pressures experienced by the test valve during the full closed cycle of the durability test while achieving a necessary threshold reverse pressure for at least a specified portion of each cycle. In some embodiments, controller 35 executes a learning algorithm 39 that automatically tunes parameters that define the waveform with which actuator 34 is driven to achieve a desired pressure profile at the valve under test.

In some embodiments controller 35 may provide operator selectable, preprogrammed wave forms. Controller 35 may provide a user interface or API 41 such that the waveforms are capable of being tailored by the user to the wave shape, amplitude and/or frequency as desired for a particular test protocol.

The pressures on valve 15 resulting from the fluid motion driven by actuator 34 may also be affected by providing one or more compliance elements. In the illustrated embodiment an upstream compliance element 37A and a downstream compliance element 37B are shown. Each compliance element may comprise, for example, an accumulator such as an air or gas pocket, a viscoelastic element such as a coated sponge, an elastic wall of a chamber, a compressible balloon, or the like. Upstream compliance element 37A may function to reduce transient pressure spikes which may have the effect of over-stressing valve 15. Downstream compliance element 37B accommodates the flow of fluid into and out of chamber 14B. In some embodiments, downstream compliance element 37B is omitted and chamber 14B is be open to atmospheric pressure.

Compliance elements may optionally be adjustable to provide enhanced control over the pressure waveform applied to the valve under test. In some embodiments the compliance elements are controlled in real time in concert with the application of fluid motion by actuator 34.

In FIG. 3 the valve under test 15 is illustrated as being of a type comprising flexible leaflets 15A that open to allow fluid flow in one direction and close to block fluid flow in the reverse direction. This is not mandatory. Apparatus such as apparatus 30 may be applied for testing heart valves having any suitable constructions.

Apparatus 30 provides a variable bypass valve 40 which helps to regulate reverse pressure on valve 15. Valve 40 may have a resistance that is set manually. In a preferred embodiment the resistance of valve 40 to the flow of fluid is automatically controlled. In the illustrated embodiment, one or more pressure sensors are provided to monitor fluid pressure and to control the opening of bypass valve 40 based on the monitored fluid pressure. In the illustrated embodiment, automatic pressure control system 19 comprises valve 40, pressure sensors 42A and 42B at pressure measuring ports 43A and 43B and a valve controller 44 that adjusts the opening of valve 40 based at least in part on pressure signals from sensors 42A and/or 42B.

In some embodiments apparatus includes a plurality of test chambers that may be applied for simultaneously testing a corresponding plurality of heart valves. In such embodiments it is not mandatory that every test chamber has its own set of one or more pressure transducers. In some embodiments one or more pressure transducers can be selectively connected to measure pressures in different test chambers by way of appropriate manifolds and valves or the like. In such embodiments a controller may implement a process of connecting one or more pressure transducers to a test chamber, monitoring pressures over one or more cycles or portions thereof, adjusting parameters controlling operation of an actuator 34 and/or bypass valve 40, and then switching the pressure transducer(s) to monitor pressures in another test chamber.

Where heart valve testing apparatus includes both a driving system 18 and a pressure control system 19 as described herein then the controllers for systems 18 and 19 may optionally be integrated. Both systems may use pressure signals from the same pressure transducer(s) for control purposes.

The operation of driving system 18 to control the inflow and outflow of fluid 16 passing through a valve under test and a bypass pathway facilitates control of the peak pressure exerted on the valve during the valve closure phase of operation. Achieving a desired threshold reverse pressure while controlling to reduce maximum pressures may reduce or eliminate false negative results over the course of a test.

Figure 4:
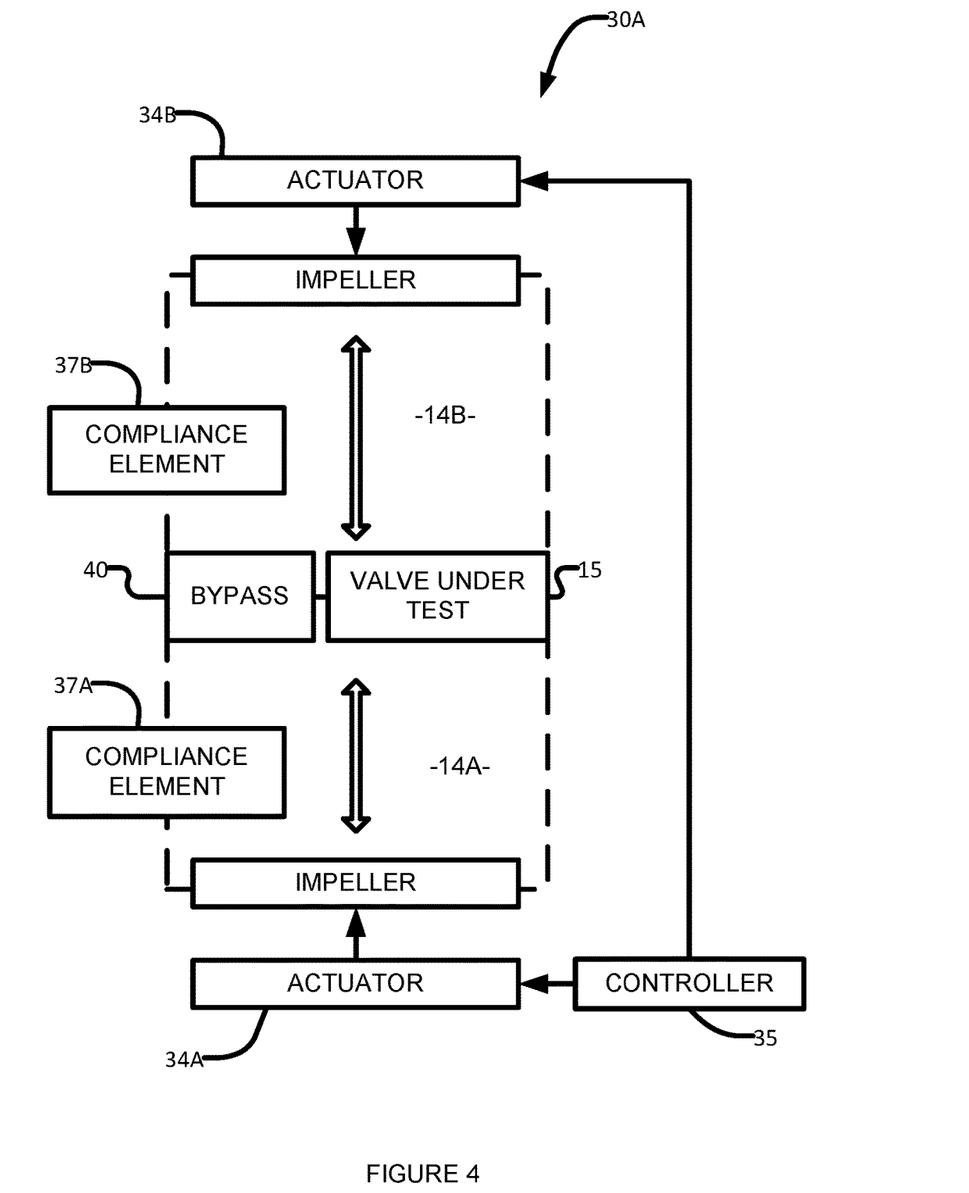
FIG. 4 is a block diagram showing valve testing apparatus according to another example embodiment which includes two actuators.

Various options and alternative embodiments may be provided. Many prosthetic cardiovascular valves are configured within stents (essentially cylindrical wire structures). Apparatus as described herein may optionally be configured to allow stent-mounted valves to be tested within tubular conduits for example. Chamber 14B may optionally be configured as a removable cartridge to allow rapid mounting of valves within the apparatus. Apparatus as described herein is not limited to having a single actuator 34. In alternative embodiments there are two or more actuators 34. For example, actuators 34 may be provided to drive fluid motion on both upstream and downstream sides of a valve under test (see e.g. apparatus 30A of FIG. 4 that includes actuators 34A and 34B).

Apparatus as described herein may be applied, for example, to testing aortic or mitral prosthetic heart valves.

Interpretation of Terms

Unless the context clearly requires otherwise, throughout the description and the claims:

"comprise," "comprising," and the like are to be construed in an inclusive sense, as opposed to an exclusive or exhaustive sense; that is to say, in the sense of "including, but not limited to".

"connected," "coupled," or any variant thereof, means any connection or coupling, either direct or indirect, between two or more elements; the coupling or connection between the elements can be physical, logical, or a combination thereof.

"herein," "above," "below," and words of similar import, when used to describe this specification shall refer to this specification as a whole and not to any particular portions of this specification.

"or," in reference to a list of two or more items, covers all of the following interpretations of the word: any of the items in the list, all of the items in the list, and any combination of the items in the list.

the singular forms "a", "an" and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present) depend on the specific orientation of the apparatus described and illustrated. The subject matter described herein may assume various alternative orientations. Accordingly, these directional terms are not strictly defined and should not be interpreted narrowly.

Data processing aspects of various embodiments of the invention may be implemented using specifically designed hardware, configurable hardware, programmable data processors configured by the provision of software (which may optionally comprise 'firmware') capable of executing on the data processors, special purpose computers or data processors that are specifically programmed, configured, or constructed to perform one or more steps in a method as explained in detail herein and/or combinations of two or more of these. Examples of specifically designed hardware are: logic circuits, application-specific integrated circuits ("ASICs"), large scale integrated circuits ("LSIs"), very large scale integrated circuits ("VLSIs") and the like. Examples of configurable hardware are: one or more programmable logic devices such as programmable array logic ("PALs"), programmable logic arrays ("PLAs") and field programmable gate arrays ("FPGAs"). Examples of programmable data processors are: microprocessors, digital signal processors ("DSPs"), embedded processors, graphics processors, math co-processors, general purpose computers, server computers, cloud computers, mainframe computers, computer workstations, and the like. For example, one or more data processors in a control circuit for a device may implement methods as described herein by executing software instructions in a program memory accessible to the processors.

Processing may be centralized or distributed.

For example, while processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

Aspects of the invention may also be provided in the form of a program product. The program product may comprise any non-transitory medium which carries a set of computer-readable instructions which, when executed by a data processor, cause the data processor to execute a method of the invention. Program products according to the invention may be in any of a wide variety of forms. The program product may comprise, for example, non-transitory media such as magnetic data storage media including floppy diskettes, hard disk drives, optical data storage media including CD ROMs, DVDs, electronic data storage media including ROMs, flash RAM, EPROMs, hardwired or preprogrammed chips (e.g., EEPROM semiconductor chips), nanotechnology memory, or the like. The computer-readable signals on the program product may optionally be compressed or encrypted.

In some embodiments, the invention may be implemented in part in software. A processor executing the software may control apparatus to execute heart valve testing methods as described herein. For greater clarity, "software" includes any instructions executed on a processor, and may include (but is not limited to) firmware, resident software, microcode, and the like. Both processing hardware and software may be centralized or distributed (or a combination thereof), in whole or in part, as known to those skilled in the art. For example, software and other modules may be accessible via local memory, via a network, via a browser or other application in a distributed computing context, or via other means suitable for the purposes described above.

Where a component (e.g. software, processor, support assembly, valve device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

It is therefore intended that the following appended claims and claims hereafter introduced are interpreted to include all such modifications, permutations, additions, omissions and sub-combinations as may reasonably be inferred.

What is claimed is:

1. Apparatus for testing replacement heart valves, the apparatus comprising:
   a mounting structure for supporting a heart valve in a passage extending between first and second chambers;
   a driving system for driving a flow of fluid through the heart valve supported on the mounting structure, the driving system comprising an actuator and a controller connected to control the actuator to provide a desired non-sinusoidal motion to a fluid impeller; and
   a pressure control system, the pressure control system comprising one or more compliance devices which can temporarily receive some fluid, one or more of the compliance devices being adjustable;
   wherein the pressure control system comprises a bypass providing a fluid connection between the first and second chambers and one or more bypass valves controllable to regulate a flow of fluid through the bypass.

2. Apparatus according to claim 1 wherein the one or more bypass valves provide resistance to fluid flow that is set manually.

3. Apparatus according to claim 1 wherein a resistance of the one or more bypass valves to fluid flow is automatically controlled.

4. Apparatus according to claim 3 comprising one or more pressure sensors wherein the controller is configured to monitor fluid pressure and to control the opening of the one or more bypass valves based on the monitored fluid pressure.

5. Apparatus according to claim 1 wherein the pressure control system comprises an automatic pressure control system comprising a bypass valve, first and second pressure sensors and a valve controller configured to adjust the opening of the valve based at least in part on pressure signals from the first and second pressure sensors.

6. Apparatus according to claim 1 wherein the pressure control system comprises one or more controlled valves operable to allow fluid to flow out of the first chamber and/or the second chamber.

7. Apparatus according to claim 1 wherein the compliance devices comprise an upstream compliance element upstream from the mounting structure.

8. Apparatus according to claim 7 wherein the upstream compliance element comprises an accumulator.

9. Apparatus according to claim 7 wherein the upstream compliance element comprises a viscoelastic element.

10. Apparatus according to claim 7 wherein the upstream compliance element comprises an elastic wall of a chamber or a compressible balloon.

11. Apparatus according to claim 1 wherein the one or more of the compliance devices is controlled in real time.

12. Apparatus according to claim 1 wherein the controller is configured to operate the driving system such that a reverse pressure on the heart valve rises to a target peak pressure somewhat in excess of a reverse threshold pressure more slowly than a sinusoidal waveform would and holds at a pressure exceeding the reverse threshold pressure for longer than a sinusoidal waveform having the same target peak pressure.

13. Apparatus according to claim 1 wherein the apparatus comprises first and second actuators, each controllable to drive fluid flow.

14. Apparatus according to claim 13 wherein the first actuator is upstream from the mounting structure and the second actuator is downstream from the mounting structure.

15. Apparatus according to claim 1 wherein the fluid impeller comprises a piston.

16. Apparatus according to claim 1 wherein the fluid impeller comprises a bellows.

17. Apparatus according to claim 16 wherein the bellows are made from inconel.

18. Apparatus according to claim 16 wherein the actuator comprises a servo motor.

19. Apparatus according to claim 18 wherein the actuator comprises a rotary motor.

20. Apparatus according to claim 19 wherein the actuator comprises a rotary-to-linear motion converter driven by the rotary motor and connected to drive the fluid impeller.

21. Apparatus according to claim 20 wherein the rotary to linear converter comprises a cam.

22. Apparatus according to claim 1 wherein the driving system comprises a position sensor connected to monitor a position of the fluid impeller.

23. Apparatus according to claim 22 wherein the controller comprises a position-feedback controller.

24. Apparatus according to claim 22 wherein the controller comprises a position and velocity feedback controller.

25. Apparatus according to claim 1 wherein the controller comprises a motion control system that is configurable to operate the actuator to provide a desired profile of position as a function of time.

26. Apparatus according to claim 25 wherein the controller is configured to provide control over one or more of: the amplitude of motions driven by the actuator; the frequency of the motions driven by the actuator; and the waveform of the wave input provided by motions driven by the actuator.

27. Apparatus according to claim 25 wherein the controller is configured to control the actuator to move the fluid impeller according a first profile having a first shape when the fluid impeller is moving in a direction such that the heart valve is closed and to move the fluid impeller according a second profile having a second shape different from the first shape when the fluid impeller is moving in a direction such that the heart valve is open.

28. Apparatus according to claim 1 wherein the controller is configured to execute an algorithm that uses feedback of pressure measured on one or both sides of the valve under test to provide proportional control of a drive wave shape to minimize pressures experienced by the test valve during a full closed cycle while achieving a threshold reverse pressure for at least a specified portion of each cycle.

29. Apparatus according to claim 28 wherein the controller is configured to execute a learning algorithm that automatically tunes parameters that define a waveform with which the actuator is driven to achieve a desired pressure profile at the valve under test.

30. Apparatus according to claim 1 wherein the controller is configured to provide a plurality of operator-selectable, preprogrammed waveforms.

31. Apparatus according to claim 30 wherein the controller comprises a user interface or API configured to permit a user to tailor the waveforms to achieve a desired wave shape, amplitude and/or frequency.

32. A method for testing replacement heart valves, the method comprising:
controlling an actuator to, in a first period, cause a flow of fluid through a heart valve under test in a forward direction wherein the heart valve is open;
controlling the actuator to, in a second period, cause a flow of fluid in a reverse direction that causes the heart valve to close and applies a reverse pressure to the heart valve; and
allowing a compliance device to temporarily receive some fluid during the testing;
wherein during the second period:
the actuator is controlled to apply a non-sinusoidal pressure waveform to the closed heart valve and the method further comprises adjusting the compliance device; and
a flow of fluid is controlled through a bypass channel to limit a reverse pressure on the heart valve.

33. A method according to claim 32 wherein controlling the flow of fluid through the bypass channel is performed in real time in response to one or more pressure sensor readings.

34. Apparatus for testing replacement heart valves, the apparatus comprising:
a mounting structure for supporting a heart valve in a passage extending between first and second chambers;

a driving system for driving a flow of fluid through the heart valve supported on the mounting structure, the driving system comprising an actuator operable to move a fluid impeller to, in a first period, cause a flow of fluid through the heart valve under test in a forward direction wherein the heart valve is open; and, in a second period cause a flow of fluid in a reverse direction that causes the heart valve to close and applies a reverse pressure to the heart valve;

a pressure control system comprising a bypass extending between the first and second chambers, a bypass valve in the bypass, the bypass valve controllable to alter a resistance of the bypass valve to fluid flow and a pressure sensor and one or more compliance devices which can temporarily receive fluid; and a controller configured to control the bypass valve in response to a pressure sensed by the pressure sensor to limit the reverse pressure applied to the heart valve in the second period.

\* \* \* \* \*